(12) United States Patent
Raybould et al.

(10) Patent No.: US 10,973,475 B1
(45) Date of Patent: Apr. 13, 2021

(54) HOLDING AND SHIELDING DEVICE

(71) Applicant: JNS Dental Products LLC, Lexington, KY (US)

(72) Inventors: Justin Raybould, Lexington, KY (US); Arnessa Craft, Lexington, KY (US)

(73) Assignee: JNS Dental Products LLC, Lexington, KY (US)

( * ) Notice: Subject to any disclaimer, the term of this patent is extended or adjusted under 35 U.S.C. 154(b) by 0 days.

(21) Appl. No.: 16/794,588

(22) Filed: Feb. 19, 2020

Related U.S. Application Data

(63) Continuation-in-part of application No. 16/601,769, filed on Oct. 15, 2019.

(51) Int. Cl.
*A61B 6/14* (2006.01)
*A61B 6/10* (2006.01)
*A61B 6/00* (2006.01)

(52) U.S. Cl.
CPC .............. *A61B 6/145* (2013.01); *A61B 6/107* (2013.01); *A61B 6/4405* (2013.01)

(58) Field of Classification Search
CPC ........ A61B 6/107; A61B 6/145; A61B 6/4405
See application file for complete search history.

(56) References Cited

U.S. PATENT DOCUMENTS

| 10,506,992 | B1* | 12/2019 | Cullen | A61B 6/42 |
| 2016/0027540 | A1* | 1/2016 | Gordon | G21F 3/00 |
| | | | | 250/515.1 |
| 2017/0303876 | A1* | 10/2017 | Lim | A61B 6/4405 |
| 2018/0214099 | A1* | 8/2018 | Martin | H01F 7/0252 |
| 2019/0336088 | A1* | 11/2019 | Gordon | A61B 6/10 |

FOREIGN PATENT DOCUMENTS

WO   WO-2017091022 A1 *   6/2017   ............... A61B 6/56

* cited by examiner

*Primary Examiner* — Mark R Gaworecki
(74) *Attorney, Agent, or Firm* — Duncan Galloway Egan Greenwald PLLC; Theresa Camoriano

(57) ABSTRACT

A holding device for use with a patient during an X-ray procedure includes an elongated arm having a proximal end and a distal end, a handle at the proximal end, and a retainer mounted on the distal end of the elongated arm for retaining something that is to be used adjacent to the patient during the X-ray procedure. An X-ray shield may be mounted on the arm between the retainer and the handle. There may be hinged joints between the retainer and the handle.

14 Claims, 21 Drawing Sheets

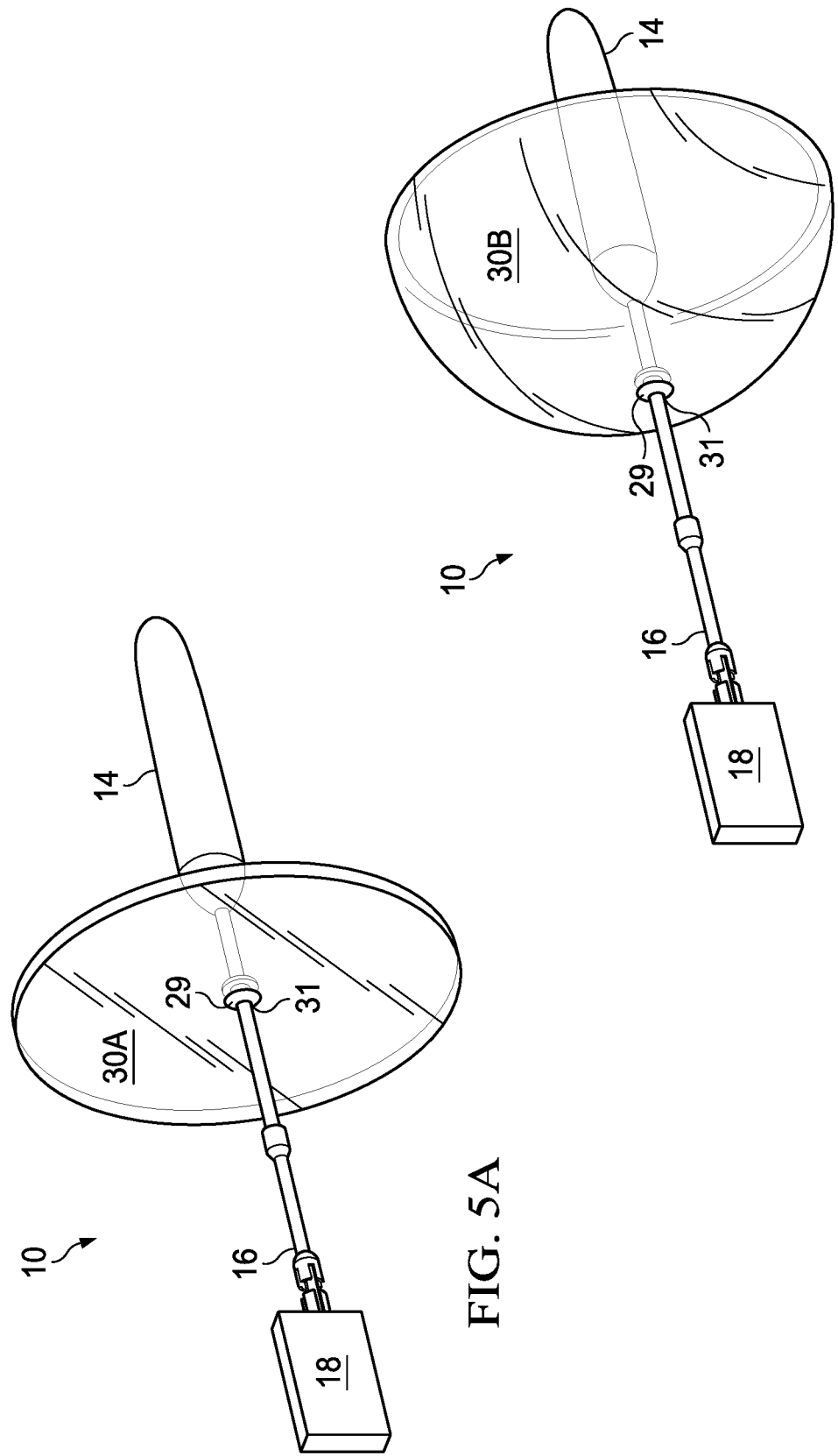

HOLDING AND SHIELDING DEVICE

BACKGROUND OF THE INVENTION

When a patient is being X-rayed, the operator tries to avoid exposure to the radiation in order to avoid the long-term effects of repeated radiation exposure. Normally, the operator stands behind the radiation source and is thereby protected. However, there are many situations, especially in pediatric dentistry, in which the operator holds an X-ray sensor in position during the X-ray, which may expose the operator's hand and lower arm to radiation. Similarly, there are situations in which the operator administers a medication to the patient during the X-ray, such as during a barium swallow test, holding a cup to the patient's mouth so the patient can drink a barium-containing compound during the X-ray procedure, which again may expose the operator to radiation.

In normal dental X-ray procedures, the operator positions the X-ray sensor assembly in the patient's mouth in specific positions depending upon whether it is desired to take, for example, horizontal or vertical bitewing X-rays, posterior periapical or anterior periapical X-rays. The patient may bite down on the assembly to hold it in place while the X-ray is being taken, or the operator may position and retain the X-ray sensor assembly in the patients mouth with a retaining device that generally consists of an elongated arm that is provided with means for holding the X-ray sensor assembly so that the operator's hand is off to the side of the patient and not in direct line of the emitted X-rays. However, the known retaining devices are bulky and often not well-received by the patient. Even when the known retaining devices are properly used, the operator's hand may be exposed to substantial scattered radiation.

In some situations, particularly in pediatric dentistry, a portable, hand held X-ray emitter is used to take the patient's X-rays. It is ideal for the operator to stand directly behind the portable hand held X-ray emitter to avoid scattered radiation as much as possible. Both when using a stationary X-ray emitter and when using a hand held X-ray emitter, if the operator manually holds the sensor assembly or some other device in the desired orientation during emission of the X-ray radiation, the operator's hand and lower arm may be subjected to undesirable doses of scattered radiation over time.

Various means are employed to minimize the exposure to radiation. For example, most portable hand held X-ray devices are provided with a radiation shield at or adjacent to the emitter end of the device. However, such shields do not protect the operator's hand and lower arm when the operator holds the X-ray sensor or other device in place in an area exposed to radiation during the X-ray.

SUMMARY OF THE INVENTION

The present invention provides an improved positioning device for holding an X-ray sensor assembly in a patient's mouth or for administering medication to a patient during an X-ray while protecting the operator from the radiation.

The positioning device allows the operator to work at the side of the patient while protecting the operator from radiation. It also provides an improved way of holding an X-ray sensor, which is less intrusive in the patient's mouth and which is adjustable to a variety of positions in the patient's mouth.

BRIEF DESCRIPTION OF THE DRAWINGS

FIGS. 5A, 5B and 5C are perspective views illustrating different embodiments of scattered radiation shields that can be used on the holder of FIG. 1;

In the Figures, the size and configuration of components may be exaggerated for clarity. The same reference numbers in different drawings represent the same component having the same function.

DESCRIPTION

Taking dental X-rays requires the insertion into the patient's mouth of an X-ray sensor to detect the X-ray radiation. The sensor may be a digital sensor or an analog sensor (i.e. a film or plate). The digital X-ray sensor can digitally communicate with a digital image processor. The X-ray sensor is held in an X-ray sensor assembly, which allows it to be held in the proper position within the patient's mouth.

Figure 1:
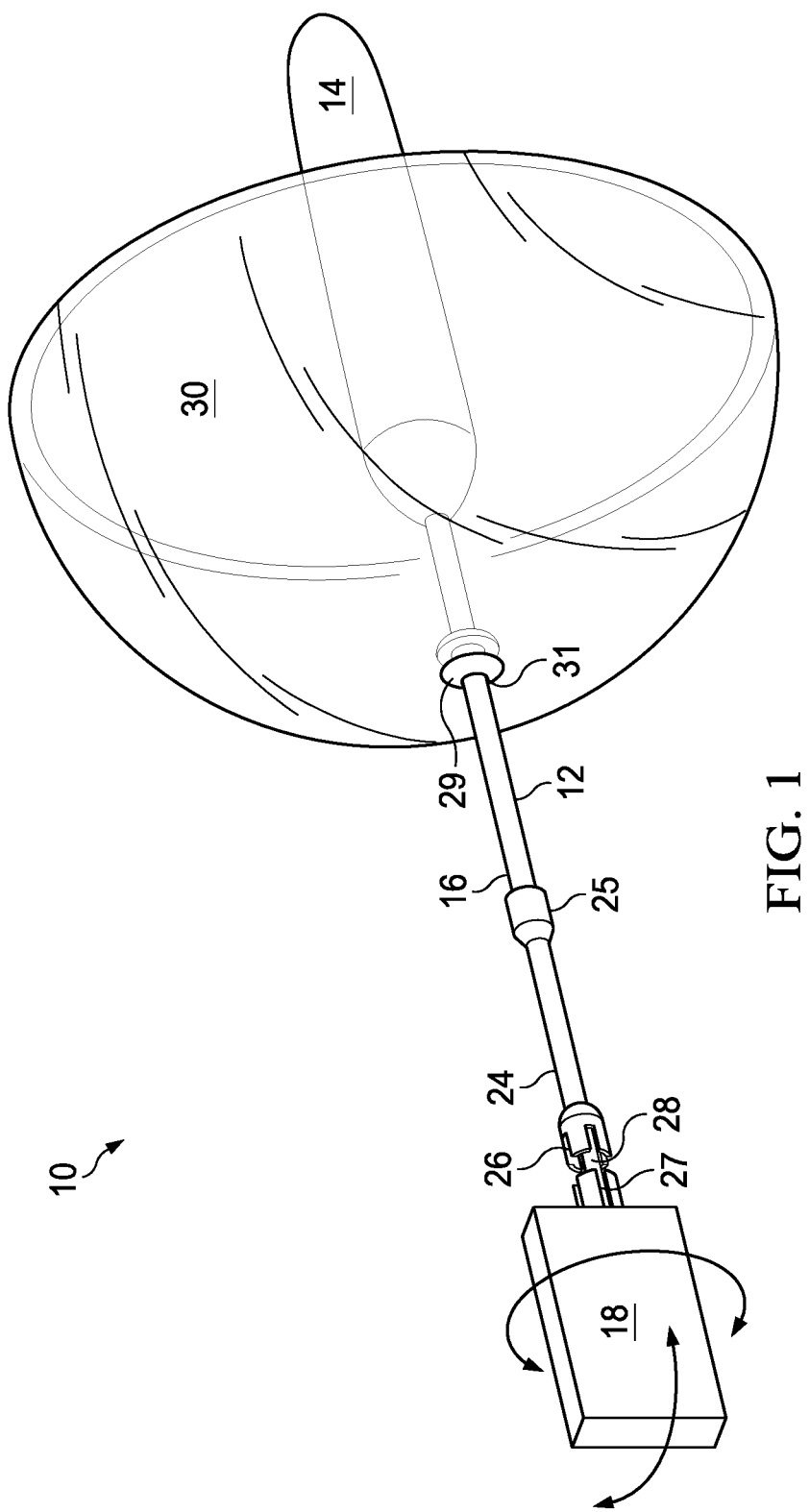
FIG. 1 is a schematic, perspective view of a first embodiment of a holding device made in accordance with the present invention.

FIG. 1 illustrates a holding device 10 that includes an elongated arm 12 having a proximal handle end 14 and a distal end 16 for attachment of an X-ray sensor assembly 18. In this embodiment, the X-ray sensor is a digital sensor. Its attachment to the arm 12 is shown in more detail in FIG. 2.

The X-ray sensor assembly 18 comprises an X-ray sensor 20 and a sensor retainer 21. The X-ray sensor 20 is secured in the sensor assembly retainer 21. A cable 22 extends from the X-ray sensor 20 to an image processing unit 23 for transmission of digital signals representative of the X-ray radiation impinging on the X-ray sensor 20 for generation of an image of the area being subjected to radiation. It will be understood that the X-ray sensor 20 alternatively may be a film plate on which the image is developed.

Figure 2:
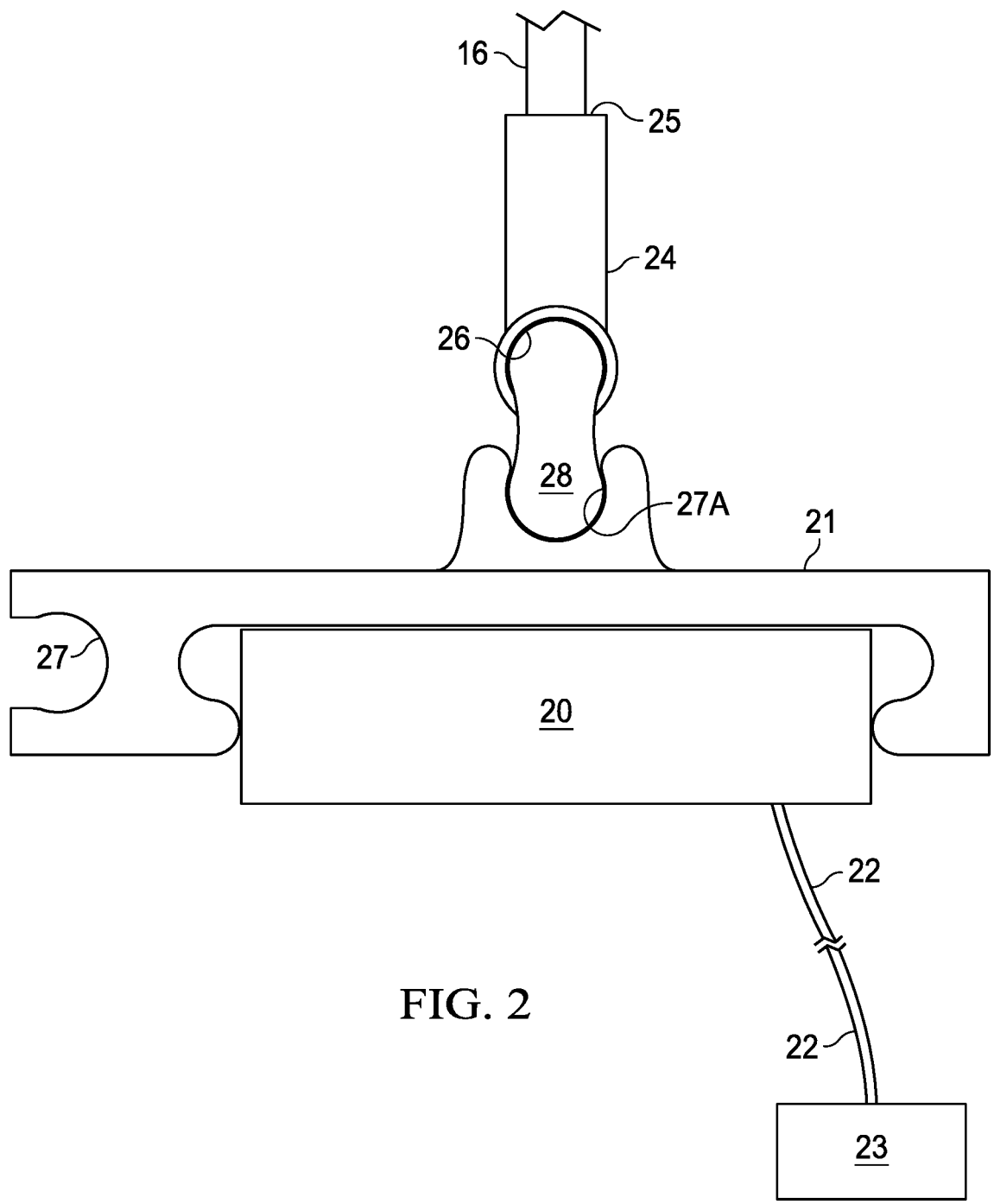
FIG. 2 is an enlarged view illustrating one way for removably attaching the X-ray sensor assembly to the holding device of FIG. 1.

The X-ray sensor retainer 21 is adapted for axial and radial movement on the arm 12 to permit positioning the X-ray sensor 20 for taking different views of the patient's mouth such as, for example, horizontal or vertical bitewing X-rays and posterior periapical or anterior periapical X-rays. A cylindrical extension 24 of the arm 12 has a first socket 25 at one end, which receives the distal end 16 of the arm 12, and a second socket 26 at the opposite end, which receives one end of a connector 28. The X-ray sensor assembly retainer 21 defines two socket members 27, 27A, for receiving the other end of the connector 28. The first socket member 27 is located on the proximal edge of the retainer 21, and the second socket member 27A is located on the rear face of the retainer 21. FIG. 1 shows the arrangement when the connector 28 is mated with the first socket member 27 at the proximal edge of the retainer 21. FIG. 2 shows the connector 28 mated with the second socket member 27A on the rear face of the retainer 21. The connector 28 has a ball formed on each end for insertion into the sockets 26 and 27 (or 27A). When the connector 28 is mated with the respective sockets, it forms a pair of ball and socket joints which movably attach the X-ray sensor retainer assembly 18 to the distal end of the arm 12. In this manner, the X-ray sensor assembly 18 can be oriented in a number of positions without the having to detach and reattach the assembly to the arm 12. Of course, other means for movably attaching the retainer 21 to the arm 12, such as other types of hinged joints, could be used as alternatives, and, in another alternative, the X-ray sensor retainer assembly 18 could be mounted non-movably to the arm 12.

Figure 6:
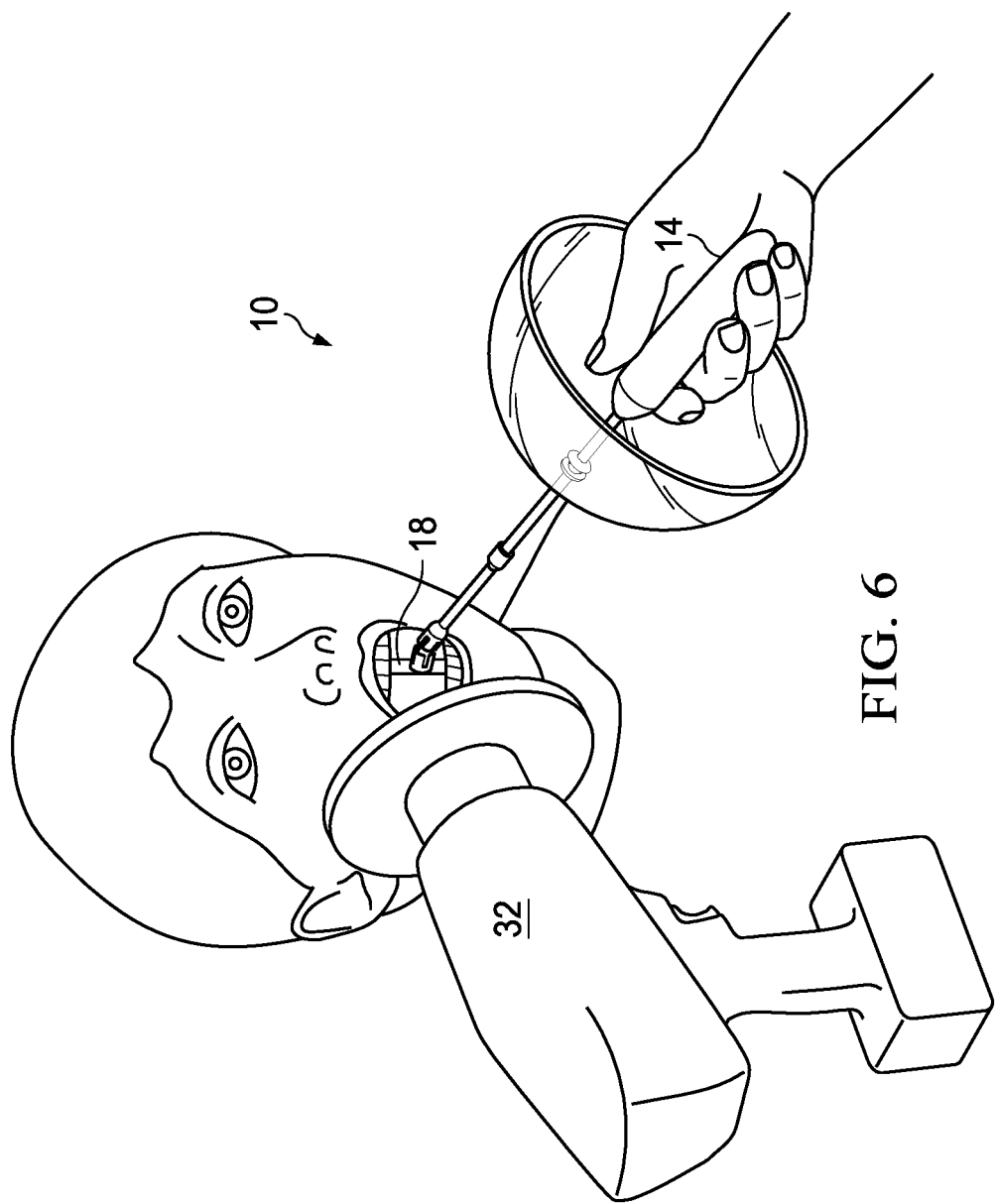
FIG. 6 is a sketch showing an operator taking an X-ray of a child's teeth utilizing the holding device of FIG. 1.

When the connector 28 is mated with the first socket member 27 at the proximal edge of the retainer 21, as in FIG. 1, the holder is less intrusive in the patient's mouth, as shown in FIG. 6.

A scattered radiation shield 30 is affixed on the elongated arm 12 to protect the operator's hand, which will be holding the handle 14 on the opposite side of the shield 30 from the X-ray sensor retainer assembly 18. The shield 30 defines a central aperture 31 through which the arm 12 extends for mounting the shield 30 on the arm. A grommet 29 secures the shield 30 on the arm 12 to prevent it from sliding during use. Alternatively, there may be a snug fit between the shield 30 and the arm, which provides enough friction that a grommet 29 is not needed. The operator may slide the shield 30 along the arm 12 to the desired position.

Figure 3:
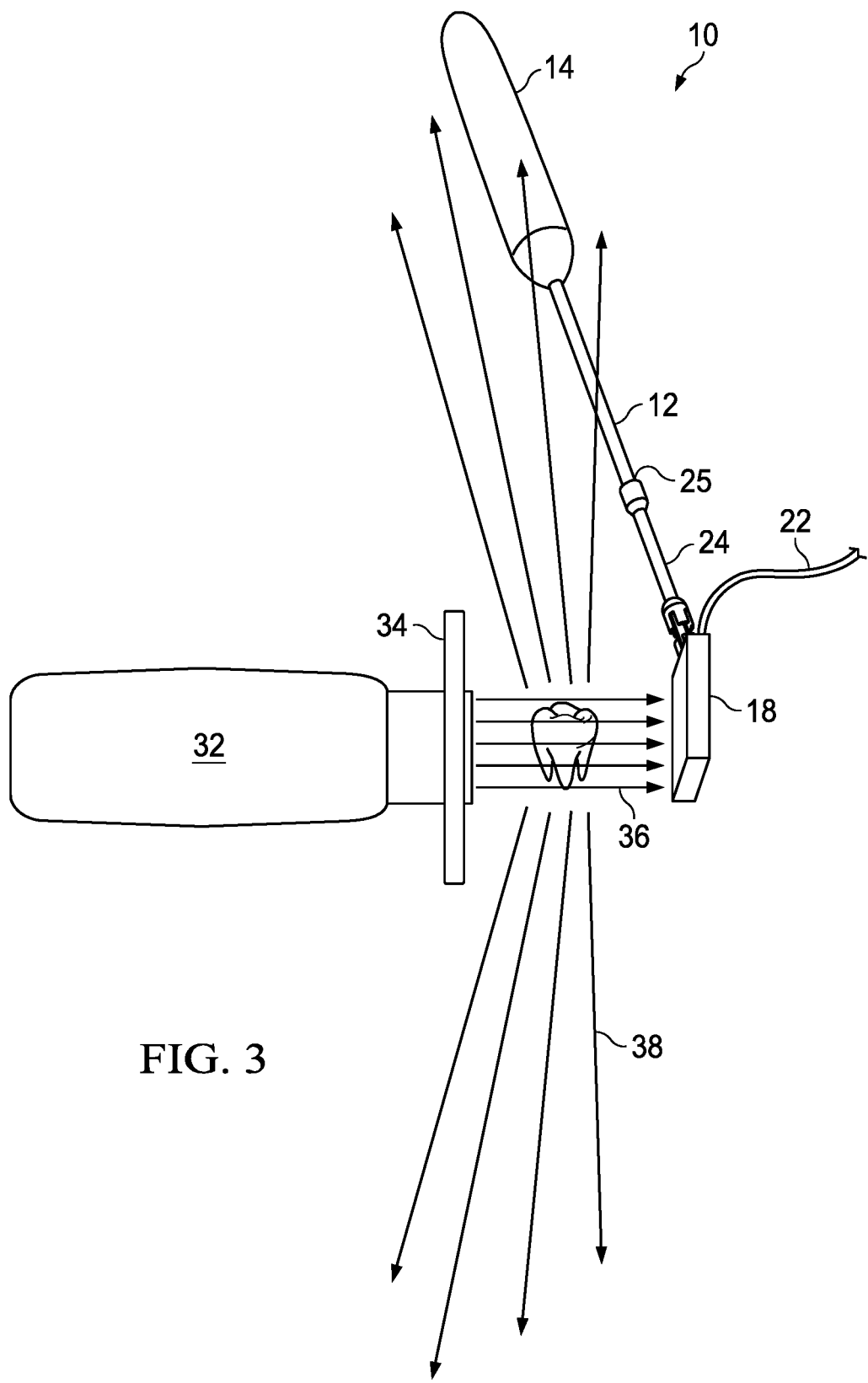
FIG. 3 is a schematic view illustrating use of the holding device of FIG. 1 without the scattered radiation shield in connection with taking an X-ray with a portable hand held X-ray emitter.
Figure 4:
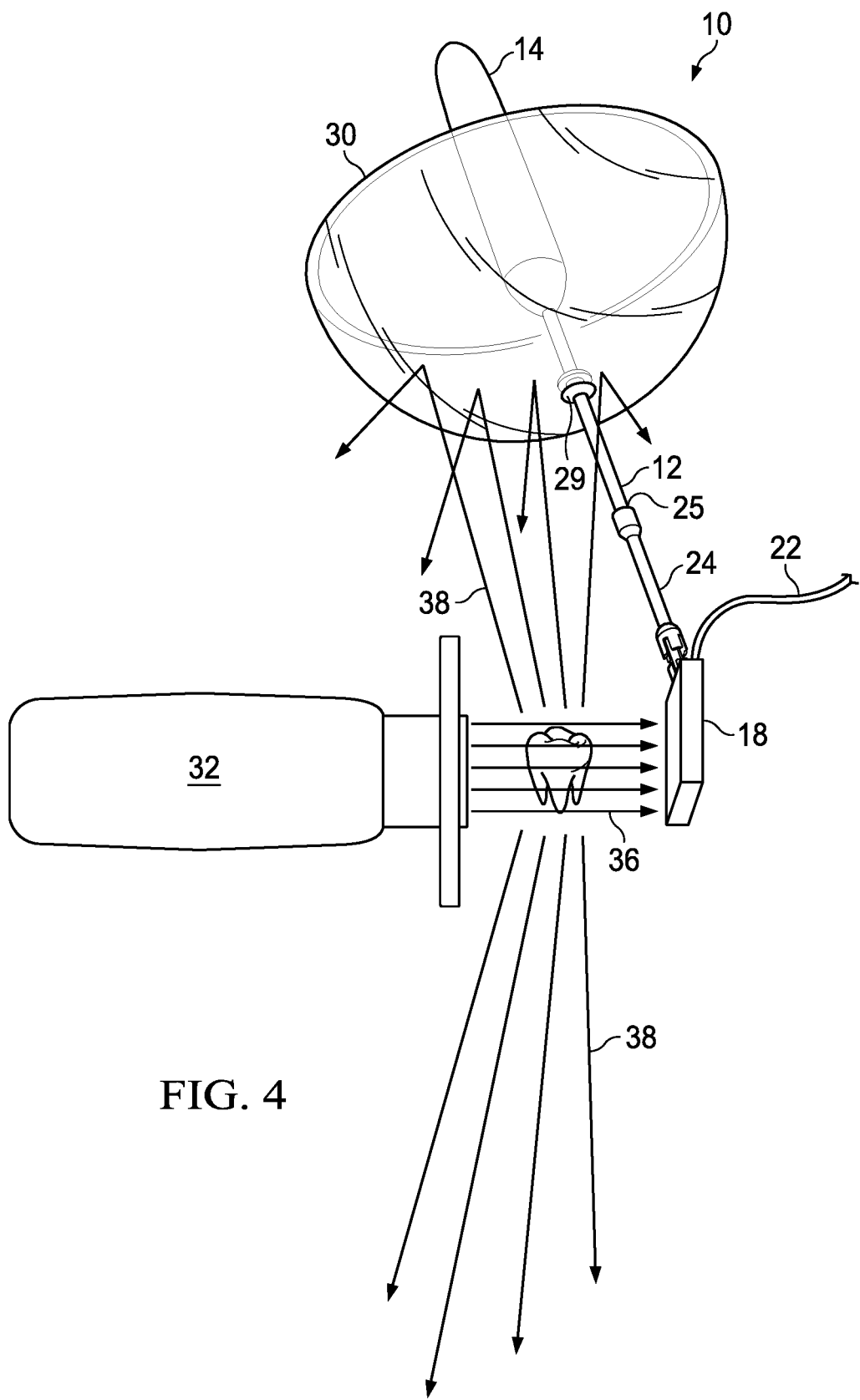
FIG. 4 is schematic view illustrating the use of the holding device of FIG. 1, with a scattered radiation shield installed on the arm of the holder.

FIG. 3 illustrates using the holding device 10 without a scattered radiation shield 30 when taking X-rays using a portable or portable hand held X-ray emitter 32 that includes a radiation shield 34 to protect the operator who is normally directly behind the emitter 32 during normal operation. The holding device 10 allows the operator to stand to one side of the of the X-ray emitter 32 while holding the sensor assembly 18 with the holding device 10 for taking X-rays of a tooth. Normally an operator stands directly behind the emitter 32 and the emitter radiation stream is focused on the target. Radiation reflected straight back from the target area is prevented from reaching the operator by absorption by the emitter shield 34. A portion of the radiation 28 is scattered to the side of the emitter 32 and is normally not a problem for the operator. However, as shown, when the operator manually positions the X-ray assembly 18 in the patient's mouth, using the holding device 10, the operator's hand on the handle 14 is exposed to the side scattered radiation. As shown in FIG. 4, the scattered radiation shield 30 on the holding device 10 protects the operator's hand holding the handle 14 during the radiation emission.

Figure 5C:
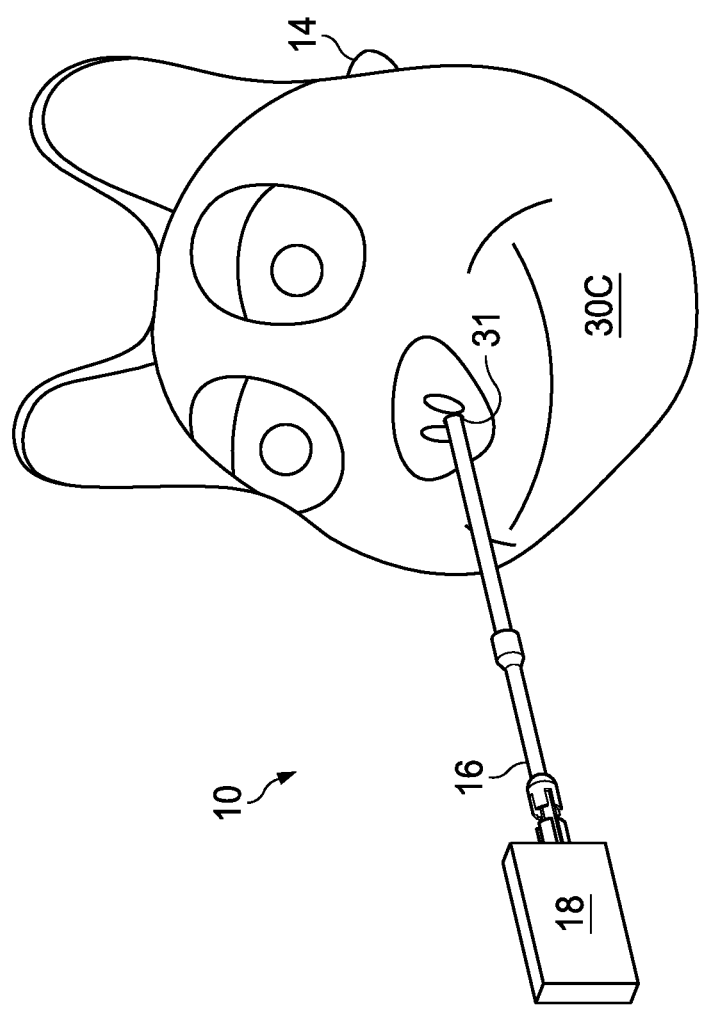

FIG. 5A, FIG. 5B and FIG. 5C illustrate various embodiments of the shield 30 (numbered as 30A, 30B, and 30C). In use, the apex of the cone-shaped shield 30B of FIG. 5B is directed towards the patient so that scattered radiation is reflected away from the operator's hand and lower arm or, depending on the composition of the shield, is absorbed. In another embodiment, shown in FIG. 5A the shield 30A is disc shaped. In another embodiment shown in FIG. 5C, the shield 30C is formed as the head of an animal or cartoon character to make taking X-rays of a child less frightening and more entertaining to the child. It will be understood that the shield 30 may take other forms such as square or rectangle.

The shield 30 should be large enough to provide shielding for the operator's hand and lower arm. The diameter of the shield preferably ranges from 6 cm. to 20 cm, although other sizes and shapes could be used.

The shield may comprise a copolymer such as polycarboxylate, polyethylene, polypropylene, polyimide, polysulfone, polvinylidine, trifluroethylene or composites thereof, or other materials with the desired properties. These materials have been found to be reflectors of X-ray radiation and to retain their properties at the energy level of dental X-rays. In addition, the copolymer may incorporate nanoparticles such as titanium, zinc, boron, boron carbide, stainless steel or the like. The incorporation of the metal nanoparticles improves the X-ray absorption properties of the shield without substantially increasing the weight of the shield. Good results have been achieved using a polycarboxylate titanium composite shield.

Preferably, the shielding composition is transparent or translucent so that the shield does not block the operator's view, and the operator can view the patient through the shield while the X-ray is being taken.

FIG. 6 illustrates the use of the holder 10 to manually retain an X-ray sensor assembly 18 while taking an X-ray of a patient's teeth. An operator (whose lower arm and hand are shown) is to one side of the X-ray emission path and grasps the handle 14 of the holder 10 with one hand while operating the emitter 32 with the other hand. The operator is standing to one side of the emitter and away from the direct radiation emission, and the scattered radiation shield 30 protects the operator's hand and arm from scattered X-ray radiation. In this fashion, the operator is not subjected to substantial cumulative X-ray radiation over a period of time.

FIGS. 7-10 show an alternative embodiment of a holder 110, similar to the holder of FIG. 5A, which uses a radiation shield 130 in the shape of a flat disc. In this embodiment, the handle 114 and arm 112 are a unitary part. The arm 112 has a square cross-section. The radiation shield 130 has a square cross-section opening 131, so the radiation shield 130 slides onto the arm 112 and is held in place by friction. A clip 113 then is slid onto the arm 112 on the opposite side of the shield 130 from the handle 114. The clip 113 defines a recess 113A, which receives the cord 122 from the digital X-ray sensor 120.

The extension 124 of the arm 112 is then fitted onto the distal end of the arm 112 by sliding the square cross-section socket 125 onto the mating square cross-section end element of the arm 112. The socket 126 on the other end of the extension 124 has a partial spherical shape. The connector 128 has a barbell shape, with a spherical-shaped ball at each end. The socket 126 includes arms that flex outwardly as the mating ball element 128A is pushed into the socket 126 until the ball 128A is received into the mating socket 126. The arms of the socket 126 then spring back to wrap more than half-way around the mating ball 128A in order to retain the ball 128A in the socket 126. The handle 114, arm 112, extension 124, and connector 128 all form a part of the elongated arm of the holder 110.

The socket 127 at the proximal edge of the retainer 121 is the same as the socket 126 on the extension 124 and similarly flexes to receive the mating ball element 128B and then springs back to retain the mating ball 128B. These two ball-and-socket connections form essentially two universal joints, which permit rotation about the axis of the arm 112 and permit pivoting in all directions about the center of each ball 128A, 128B. This allows for a wide range of adjustment positions that permit the operator to adjust the position of the sensor 120 to best locate the sensor 120 in the patient's mouth. Some of the various positions are shown in later figures.

The sensor 120 has a flat, rectangular shape. The retainer 121 has a flat, rectangular-shaped face that lies flat against the flat face of the sensor 120, and it has flexible fingers 129, fixed to the back portion, that wrap around the edges of the sensor 120 to hold the sensor 120 in position when the rectangular face of the sensor 121 abuts the back of the retainer 121. The fingers 129 flex to enable the sensor 120 to snap into the retainer 121 and be retained on the retainer 121 with the flat face of the sensor lying against the flat back portion of the retainer.

Figure 7:
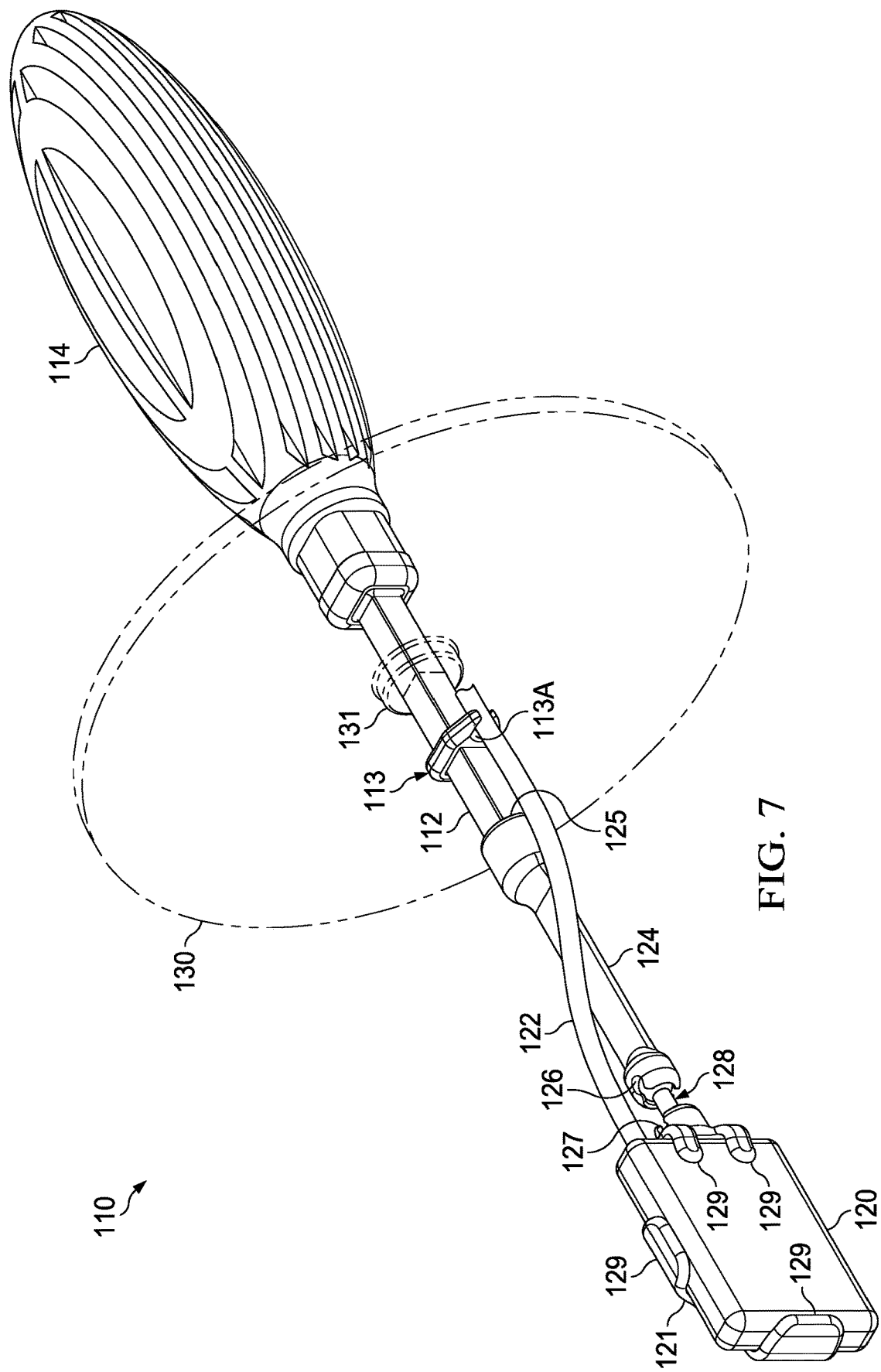
FIG. 7 is a perspective view of an alternative holding device, with an X-ray sensor snapped into the holding device and with a radiation shield shown in phantom.
Figure 8:
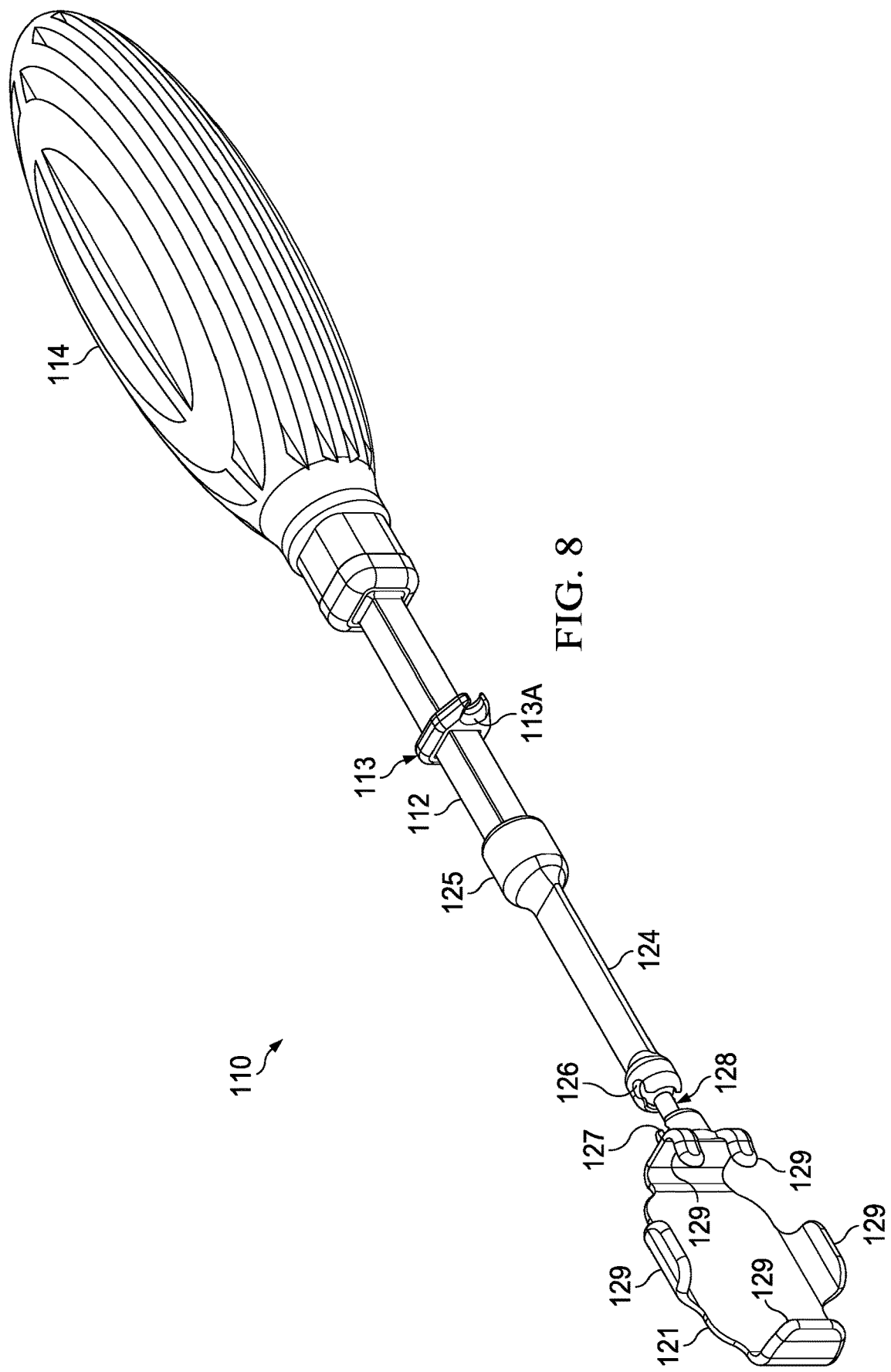
FIG. 8 is the same view as FIG. 7 but with the X-ray sensor and radiation shield removed for clarity.

The flat, rectangular-shaped face of the retainer 121 has a perimeter edge, which includes the proximal edge where the socket 127 is located. The flexible fingers 129 are located around the perimeter edge of the retainer 121, as shown in FIGS. 8 and 9, and the flexible fingers 129 snap onto the edge of the sensor 120 when the sensor 120 is snapped into the flexible fingers 129, as shown in FIGS. 7 and 9C.

Figure 9A:
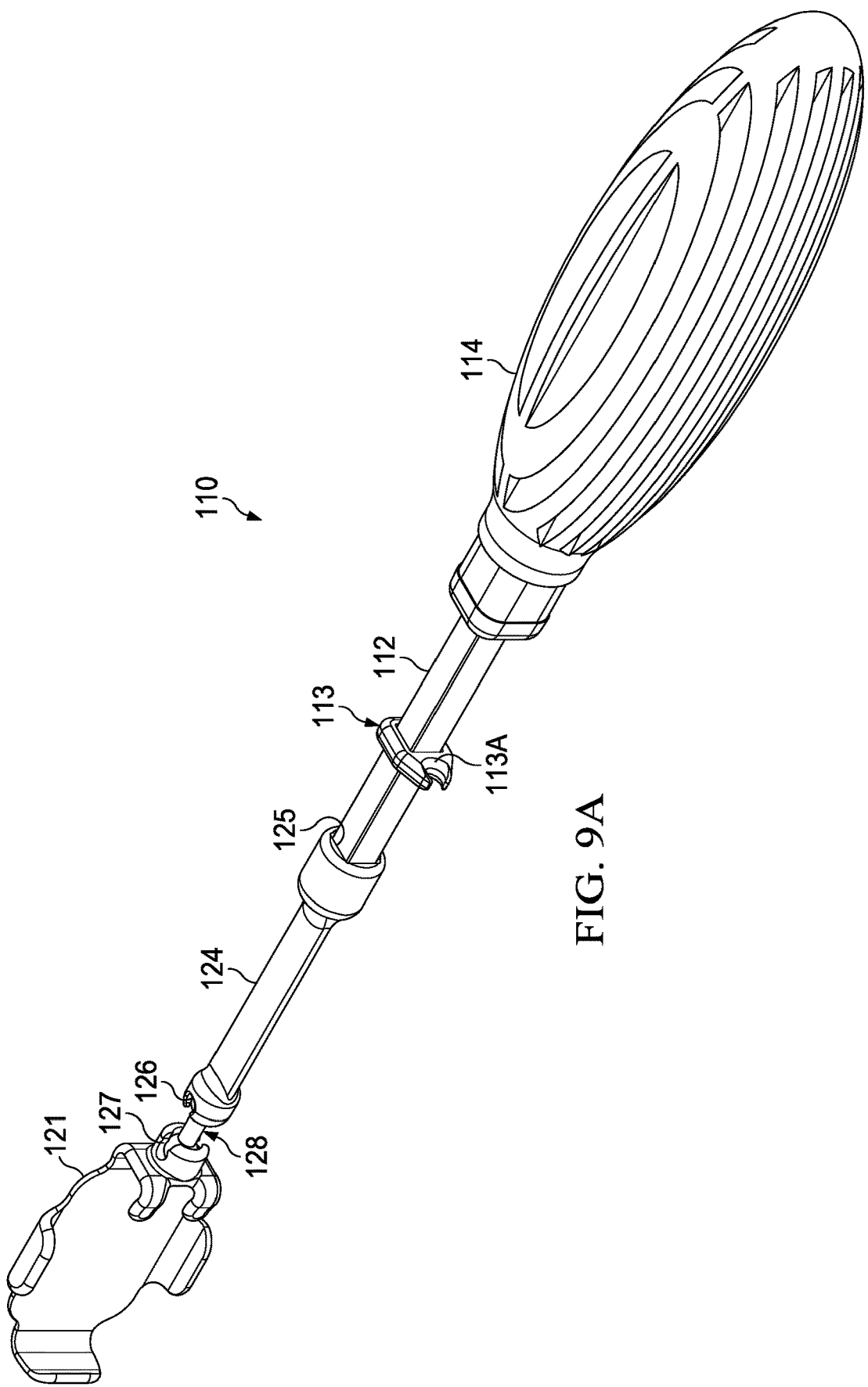
FIG. 9A shows the same holding device as FIG. 8 but from the opposite end.
Figure 9B:
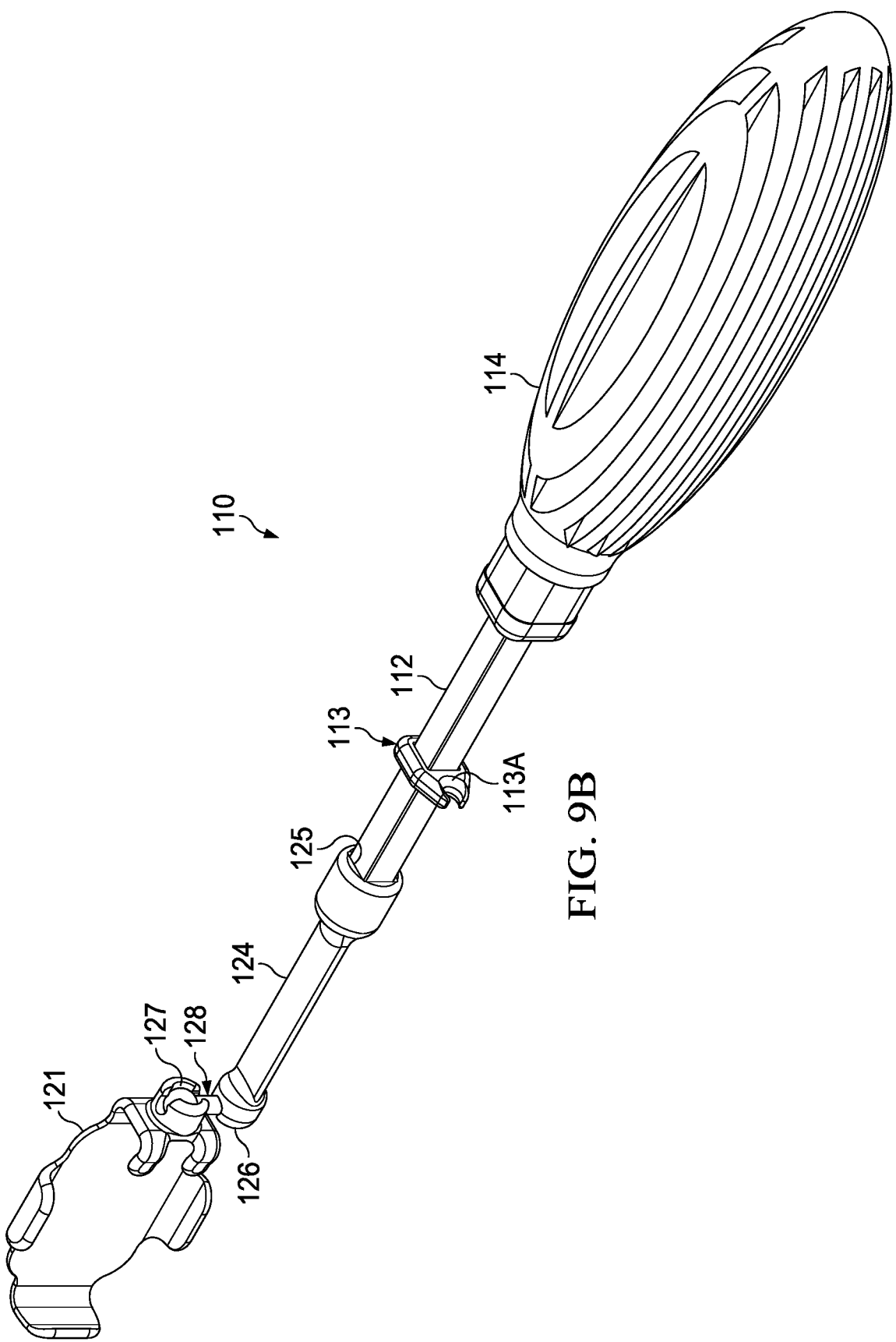
FIG. 9B is the same view as FIG. 9A, but with the holding device moved to a different position.

FIG. 9B shows the holder 110 of FIG. 9A, but with the ball and socket joints having pivoted to a different position. The balls 128A, 128B and their respective sockets 126, 127 are sized and made of materials that provide a snug fit with enough friction, so that, once the operator moves them to a desired position, they will remain in that position until the operator moves them to a different position.

Figure 9C:
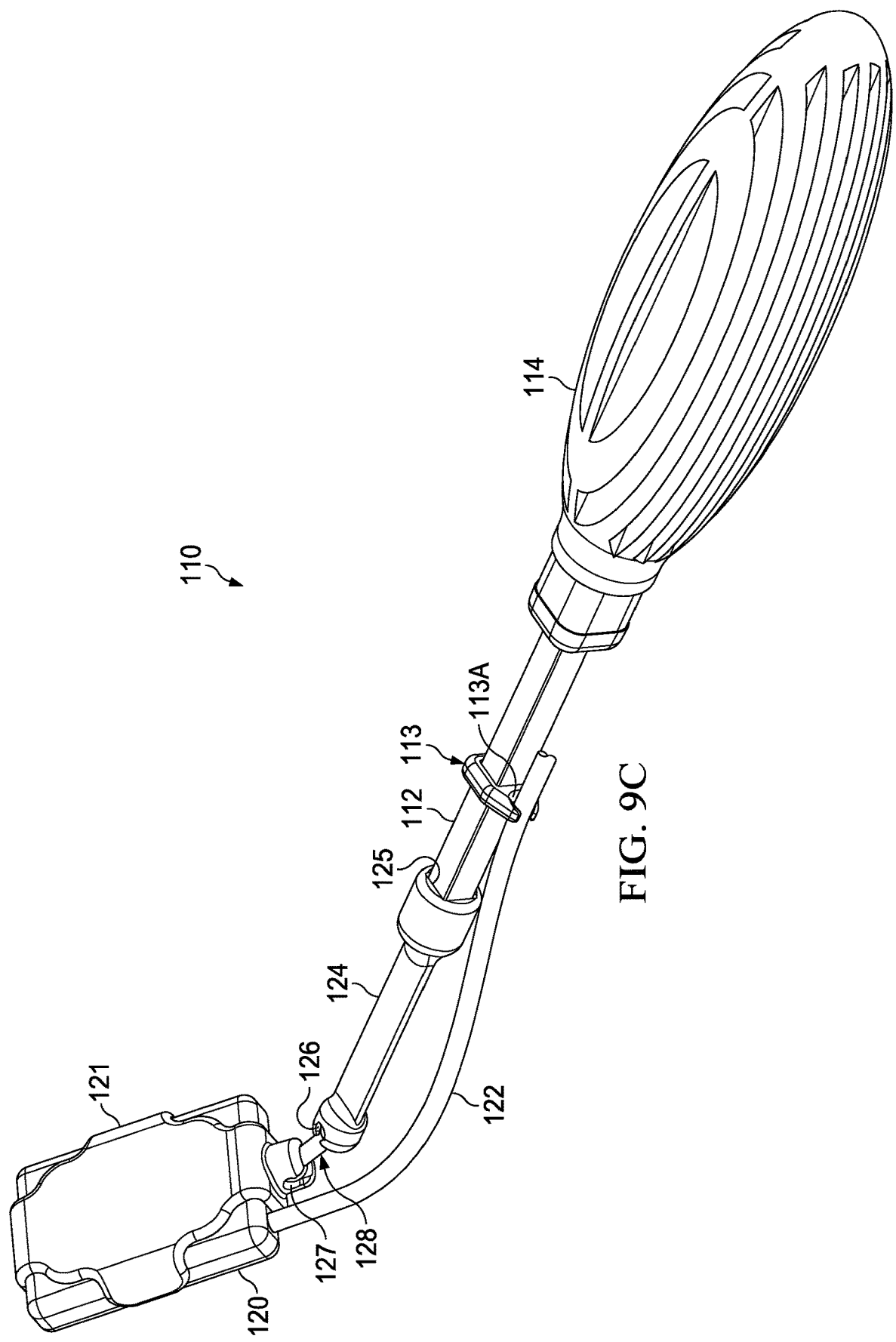
FIG. 9C is the same view as FIG. 9A, but with an X-ray sensor installed and with the holding device moved to another different position.

FIG. 9C shows the holder 110 pivoted to another different position.

Figure 10:
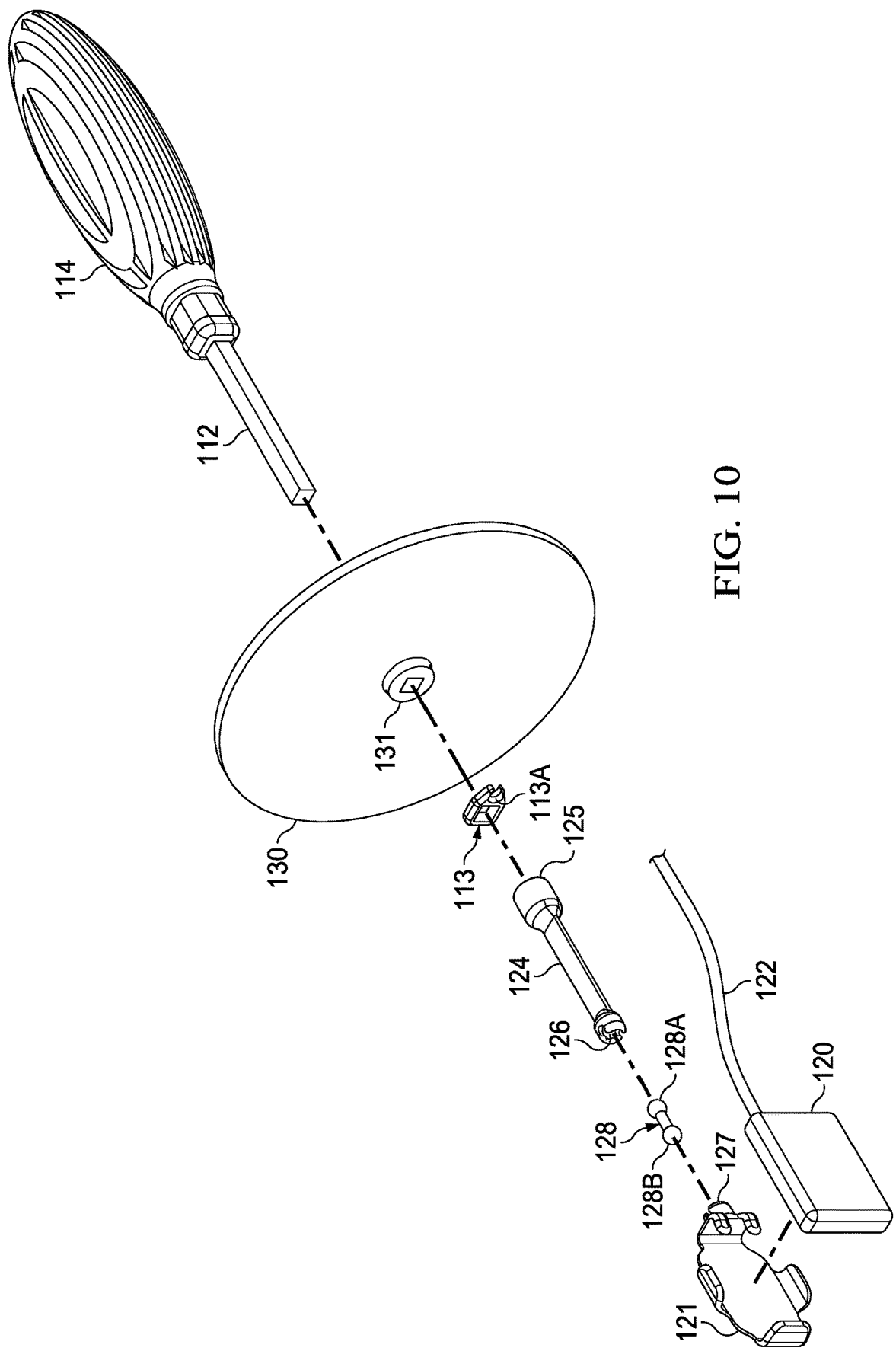
FIG. 10 is an exploded perspective view of the device of FIG. 7.

FIG. 10 is an exploded perspective view of the holder 110.

Figure 11:
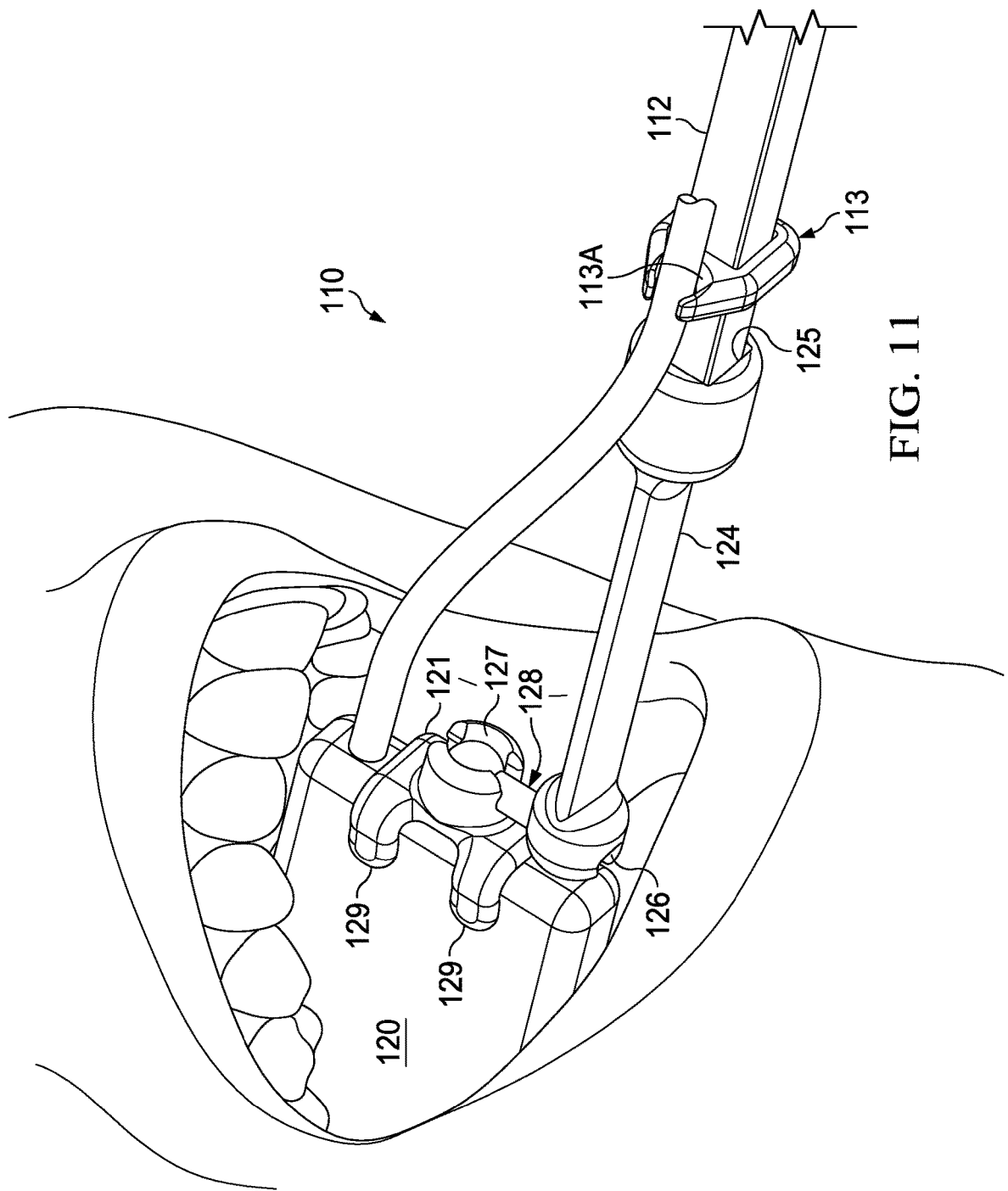
FIG. 11 shows the holding device of FIG. 7-10 inserted into a patient's mouth.

FIG. 11 shows the holder 110 inserted into a patient's mouth and moved to a desired position for taking an X-ray in that patient's mouth. It should be noted that, since the retainer 121 is very thin and conforms to the shape of the X-ray sensor 120, and since the socket 127 is on the proximal edge of the retainer 121, the holder 110 takes up very little room in the patient's mouth, requiring only slightly greater room than the X-ray sensor 120 itself. Also, since the ball and socket joints permit the arm 112 to project out of the patient's mouth from a position that is axially offset from the socket 127, as shown in FIG. 11, the holder 110 allows for a wide range of positions that interfere very little with the patient's mouth.

Figure 12A:
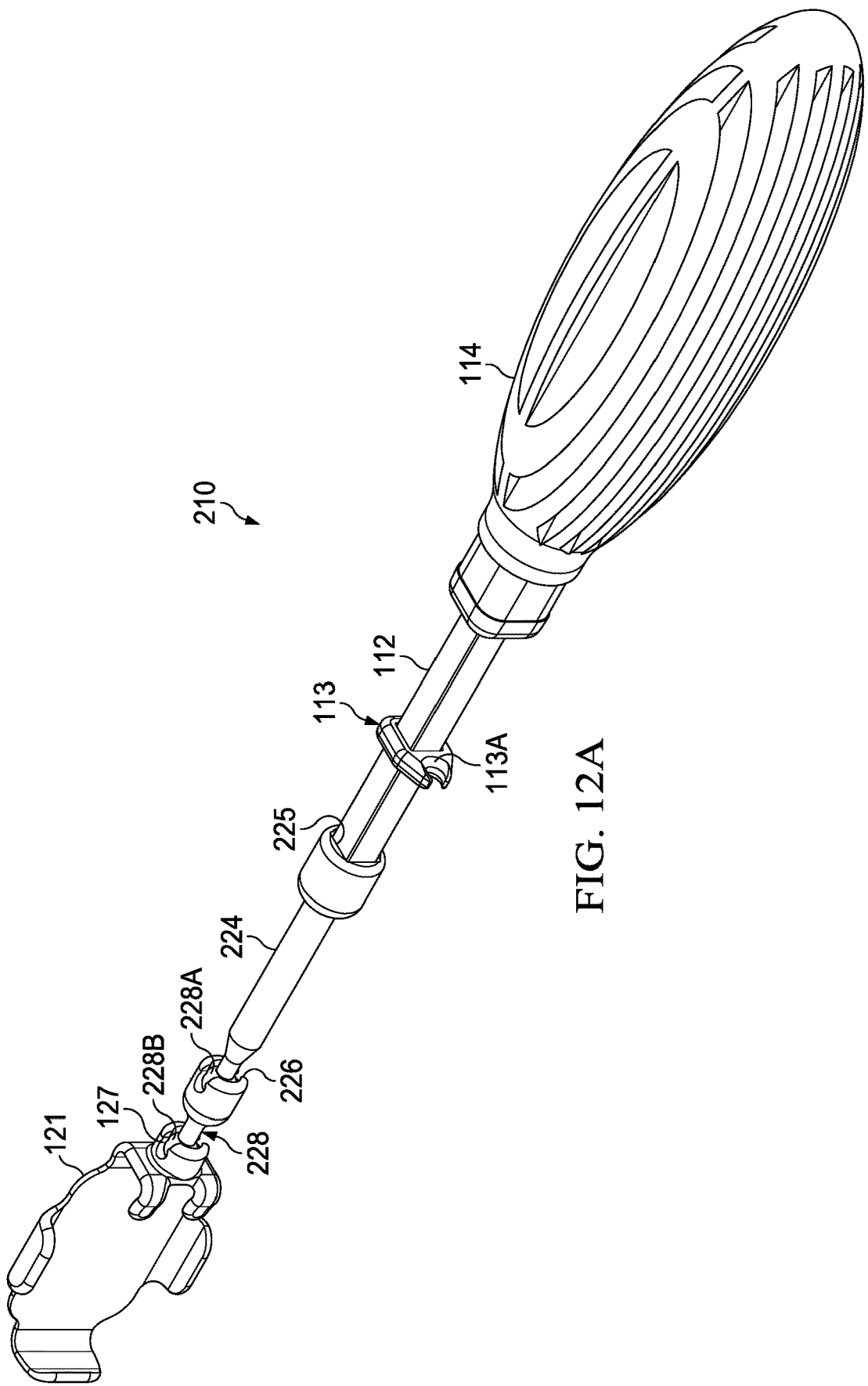
FIG. 12A shows an alternative holding device, similar to the device of FIGS. 7-10, but with one of the ball and socket joints reversed and with the radiation shield removed for clarity.

FIG. 12A shows an alternative embodiment of a holder 210, which is similar to the holder 110 of FIGS. 7-11 except that the positions of the ball and socket at the proximal ball and socket joint have been reversed. In this case, the proximal end of the extension 224 connects to the arm 112 in the same manner as the previous embodiment, but the distal end of the extension 224 has a ball 228A instead of the socket 126, and the connector 228 has a socket 226 at its proximal end that receives the ball 228A. The distal end of the connector 228 is the same as the previous embodiment, with a ball 228B that is received in the socket 127 at the proximal edge of the retainer 121.

Figure 12B:
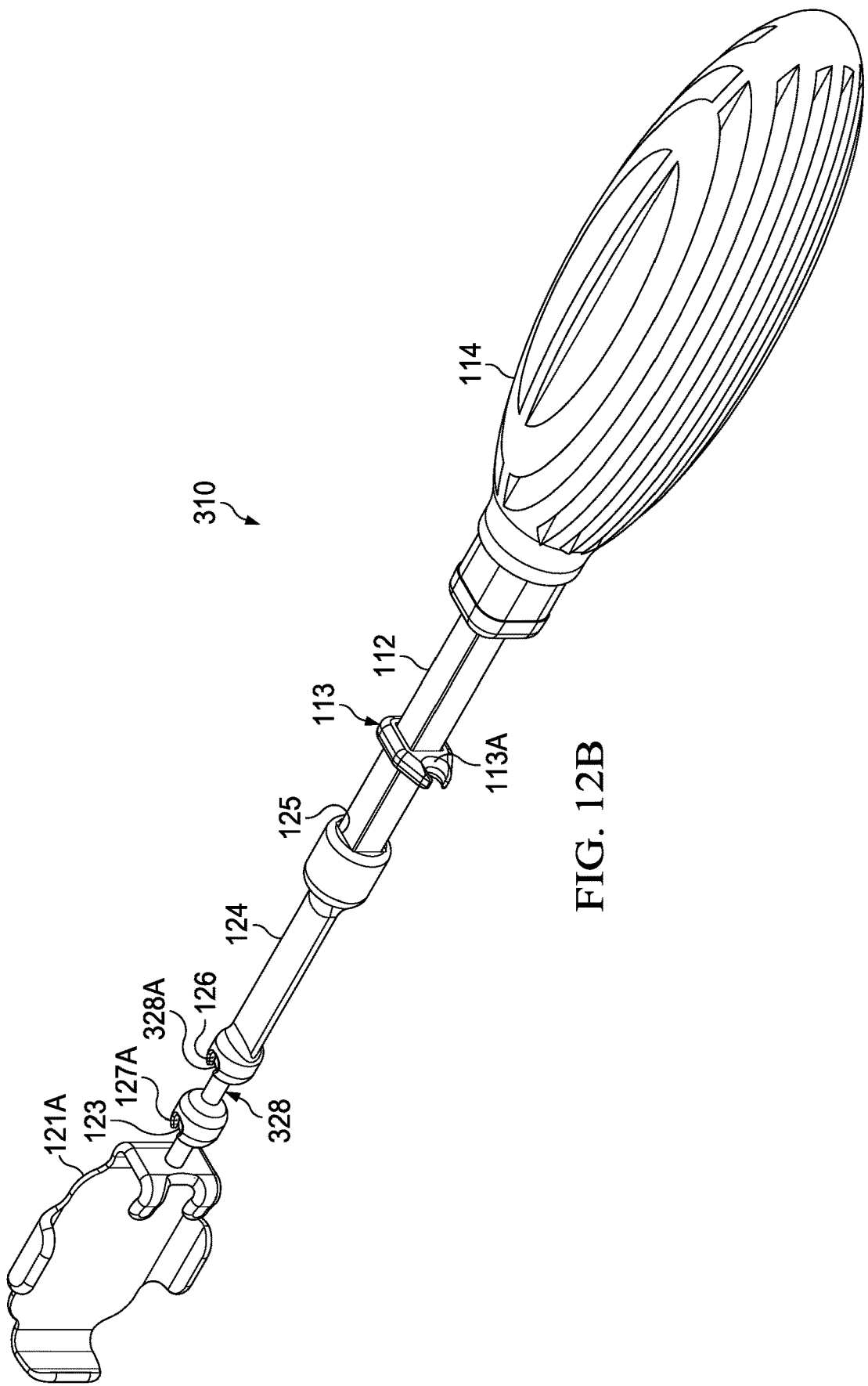
FIG. 12B shows another alternative holding device, similar to the device of FIGS. 7-10, but with another of the ball and socket joints reversed and with the radiation shield removed for clarity.

FIG. 12B is another alternative embodiment of a holder 310, which is the same as the embodiment of FIGS. 7-11, except that the ball and socket at the distal end of the connector 328 are reversed, with the retainer 121A having a ball 123 projecting out of its proximal edge, and the connector 328 having a socket 127A at its distal end which receives the ball 123. The proximal end of the connector 328 has a ball 328A, which is received in the socket 126 of the extension 124. It alternatively would be possible to make the connector have sockets at both ends, which receive respective balls at the distal end of the extension and at the proximal end of the retainer.

Figure 12C:
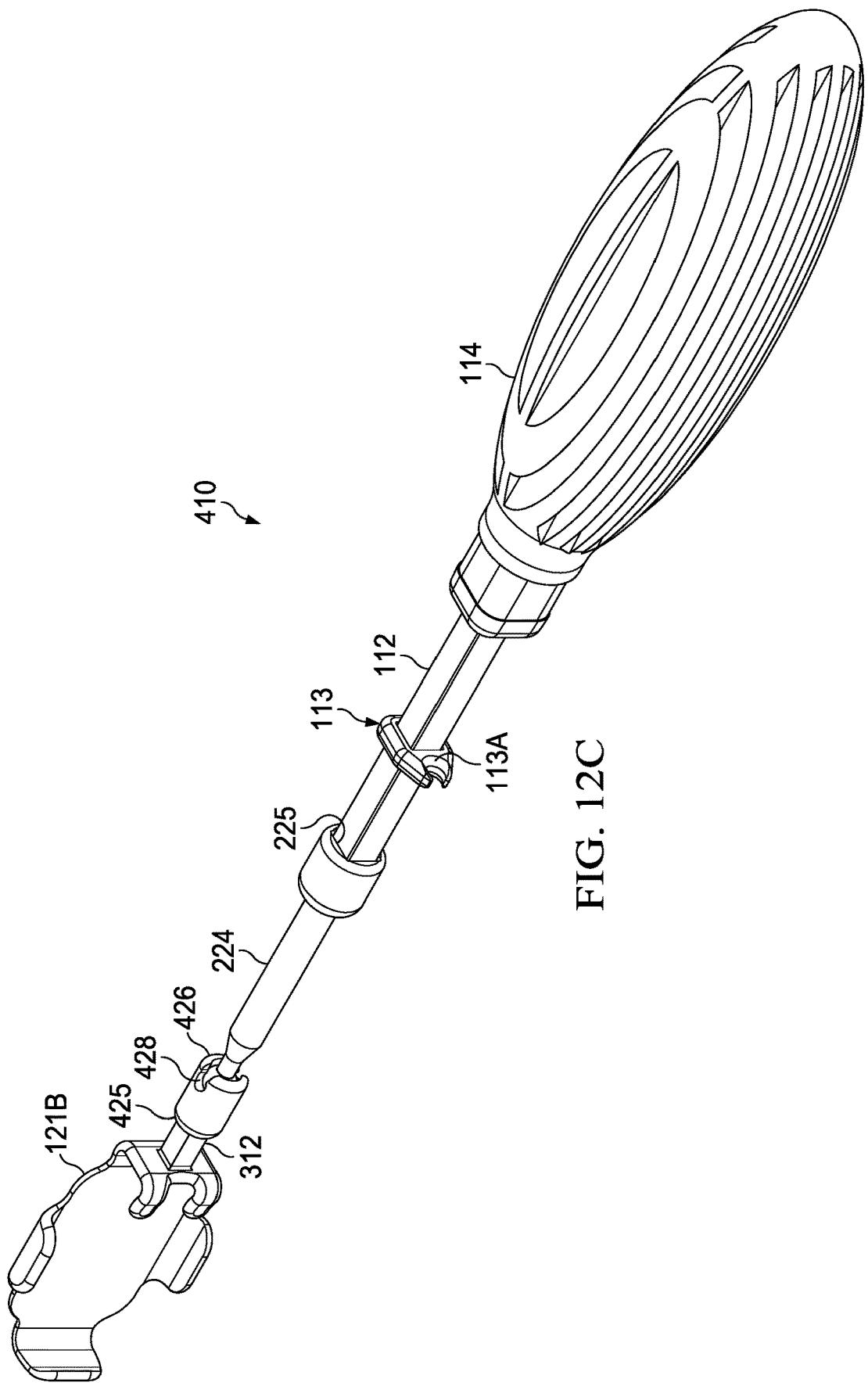
FIG. 12C shows another alternative holding device, similar to the device of FIGS. 7-10, but with only a single ball and socket joint.

FIG. 12C is another alternative embodiment of a holder 410, which is the same as the embodiment of FIGS. 7-11, except the holder 121B has a square cross-section projection 312 at its proximal end, which is received in a square cross-section socket 425 at the distal end of the connector 428. The proximal end of the connector 428 has a partial spherical recess 426 which receives the ball at the end of the extension 224.

Figure 13A:
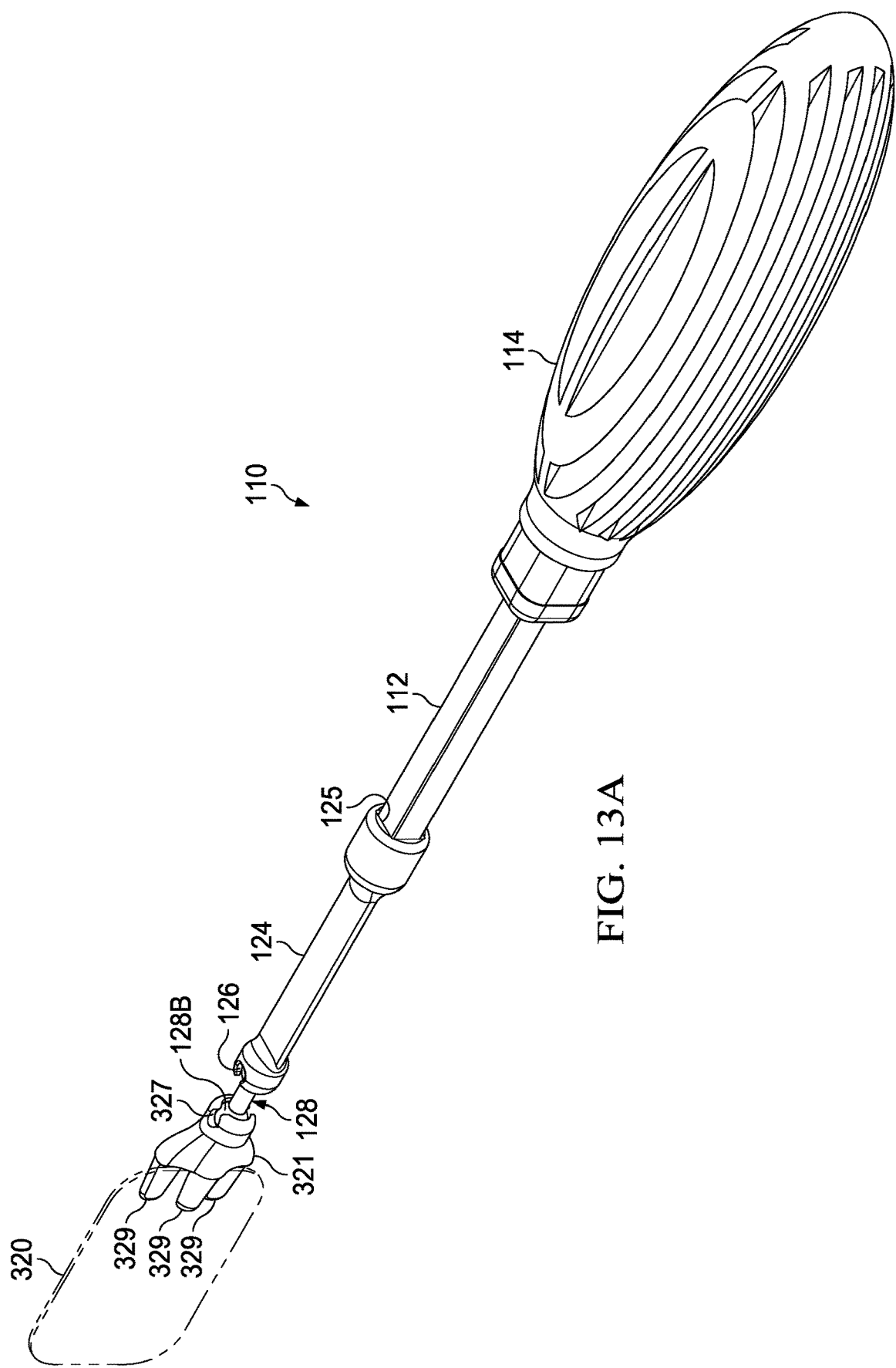
FIG. 13A shows another alternative holding device, similar to the device of FIGS. 7-10 but designed to receive an X-ray sensor in the form of a plate.
Figure 13B:
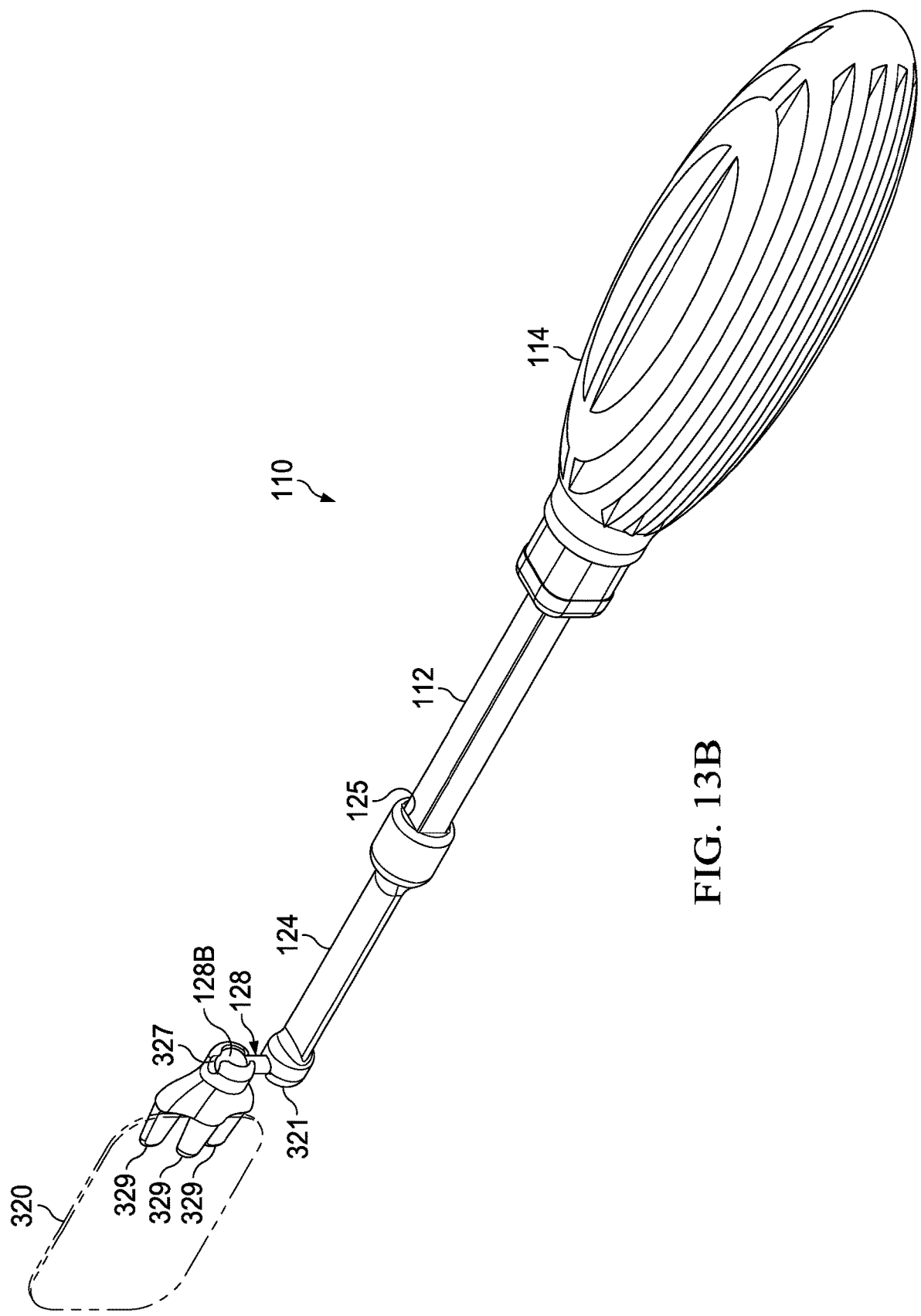
FIG. 13B shows the holding device of FIG. 13A but moved to a different position.
Figure 13C:
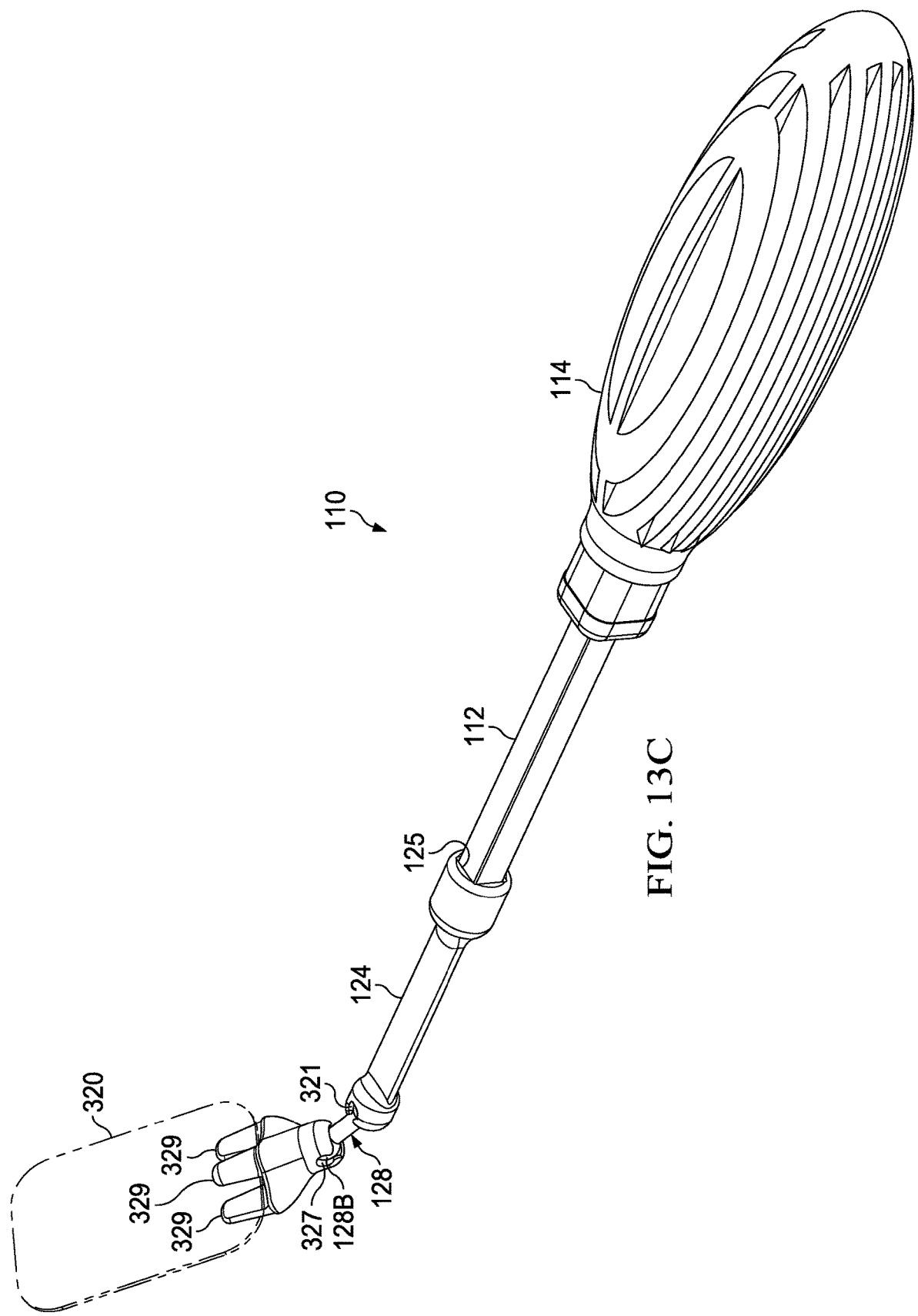
FIG. 13C shows the holding device of FIG. 13A but moved to another different position.

FIGS. 13A-C show another alternative embodiment, which is the same as the holder 110 of FIGS. 7-11, except that a retainer 321 replaces the retainer 121. This retainer 321 is designed to receive an X-ray plate 320 by sliding the flat, rectangular X-ray plate 320 into the fingers 329. Two of the fingers 329 lie in the same plane, and their inner surfaces define a flat face against which the flat X-ray plate 320 rests. The proximal edge of the retainer 321 defines a socket 327. As in the embodiment of FIGS. 7-11, the ball of the connector 128 snaps into the socket 327 at the proximal edge of the retainer 221, so the arm 112 connects to the retainer 321 at the proximal edge of the retainer 221, and a large range of flexibility of positions is provided in order to adjust the position of the X-ray plate in the patient's mouth with very little interference with the patient's mouth. FIGS. 13B and 13C show the holder having been moved to alternative positions.

Figure 14:
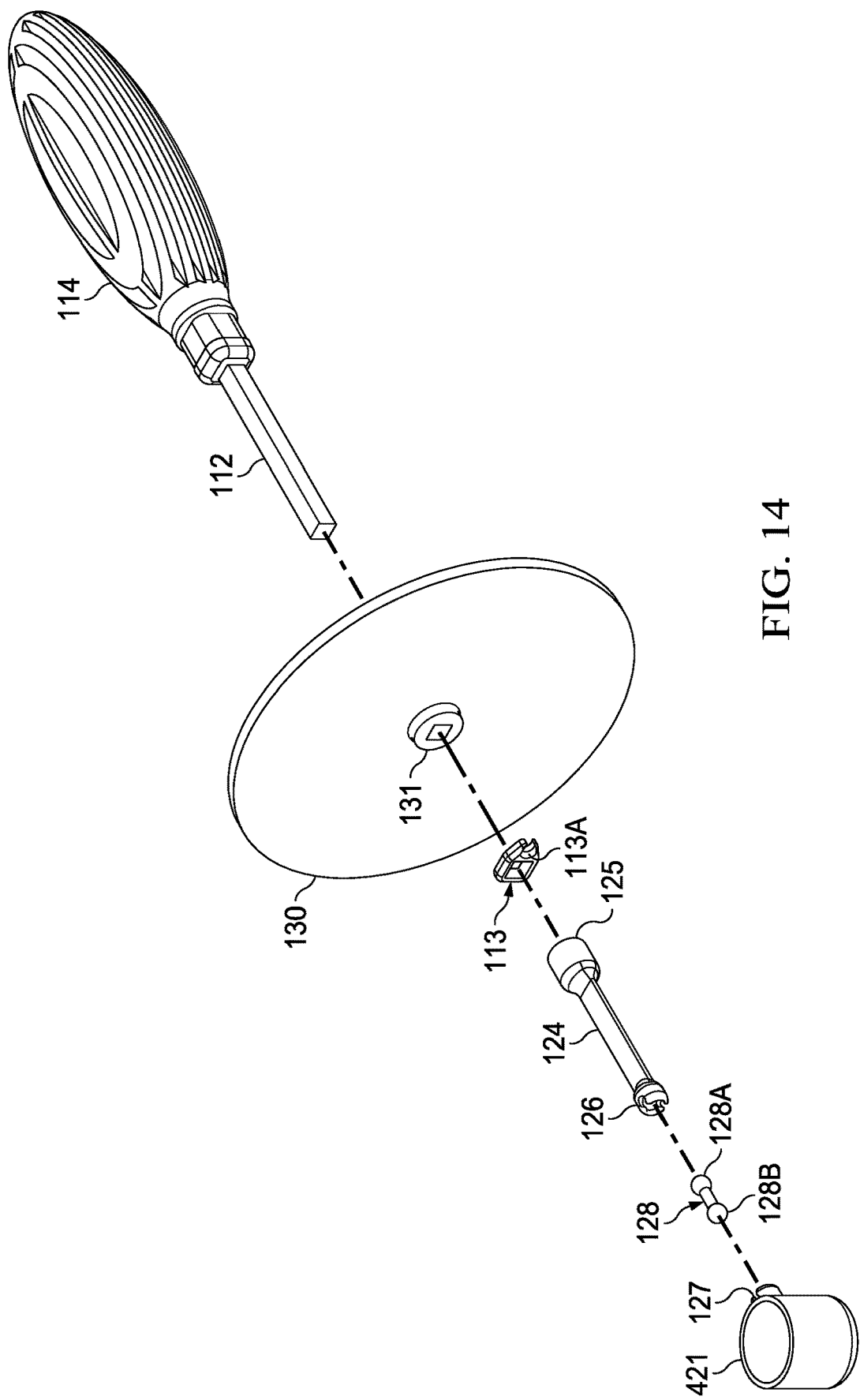
FIG. 14 shows another alternative holding device, similar to the device of FIGS. 7-10, but with a cup-type retainer on the end for retaining medication to be administered to a patient instead of the X-ray sensor retainer.

FIG. 14 shows another alternative embodiment that is the same as the embodiment of FIGS. 7-11, except that a cup-type retainer 421 replaces the retainer 121. This arrangement allows an operator to administer medicine to a patient while an X-ray is being taken, while protecting the operator from the radiation. The operator places the medication into the cup 421, then holds the handle 114 and pours the medication from the cup 421 into the patient's mouth as the X-ray is being taken. In this case, no X-ray sensor is being placed into the patient's mouth but rather the X-ray sensor is stationary and located on the opposite side of the patient from the emitter. This arrangement may be used, for example, for a barium swallowing test.

A cup-type retainer, X-ray sensor retainer, or other type of retainer may alternatively be mounted in a fixed position on the extension 124. The parts of the holder may be made so they can be disinfected in an autoclave, or some or all of the parts may be disposable so they are thrown out after each use.

It will be understood that this invention may be used with a portable hand held X-ray emitter devices and with a stationary X-ray emitter.

While the invention has been described in detail in the drawings and foregoing description, the same is to be considered as illustrative only and not restrictive in character. Many modifications and changes will be obvious to those of ordinary skill in the art and will be within the scope of the invention as claimed.

What is claimed is:

1. A holding device for use with a patient during an X-ray procedure, comprising:
    an elongated arm having a proximal end and a distal end;
        a handle at said proximal end; a retainer mounted on the distal end of said elongated arm; and an X-ray shield mounted on said arm between said retainer and said handle;
    wherein said retainer defines a flat face and a proximal edge; wherein said retainer is mounted on said arm at said proximal edge of said retainer by a first ball and socket joint, with one of a ball and socket being at said proximal edge of said retainer and the other of said ball and socket being at the distal end of said arm.

2. A holding device for use with a patient during an X-ray procedure as recited in claim 1, wherein said retainer is sized and shaped to retain an X-ray sensor, and wherein said socket includes arms that flex outwardly to receive said ball and then spring back to retain said ball in said socket with enough friction so that, once said retainer is moved to a desired position relative to the arm and is released, the retainer will remain in that position.

3. A holding device for use with a patient during an X-ray procedure as recited in claim 2, and further comprising a second ball and socket joint between said handle and said retainer, said second ball and socket joint being spaced in the proximal direction from said first ball and socket joint.

4. A holding device for use with a patient during an X-ray procedure as recited in claim 3, wherein said retainer defines a perimeter edge, which includes said proximal edge, and further comprising a plurality of flexible fingers on said perimeter edge for snapping onto the edge of an X-ray sensor for retaining the sensor on the retainer.

5. A holding device for use with a patient during an X-ray procedure, comprising an elongated arm having a distal end and a proximal end, with a handle at said proximal end; a cup-shaped retainer mounted on said distal end of said elongated arm at a first ball and socket joint a second ball and socket joint spaced in the proximal direction from said first ball and socket joint; and an X-ray shield mounted on said arm in the proximal direction from said second ball and socket joint.

6. A holding device for use with a patient during an X-ray procedure as recited in claim 5, wherein said first ball and socket joint includes a first ball and a first socket including arms that flex outwardly to receive said first ball and then spring back to retain said first ball in said first socket.

7. A holding device for use with a patient during an X-ray procedure, comprising:
    a retainer for holding an X-ray sensor, said retainer defining a flat face and a perimeter edge including a proximal edge; a plurality of flexible fingers along said perimeter edge for snapping onto the edge of a flat sensor to be retained on said retainer and one of a ball and a socket on said proximal edge.

8. A holding device for use with a patient during an X-ray procedure as recited in claim 7, wherein said one of a ball and a socket on said proximal edge is a socket including arms that are adapted to flex outwardly to receive a ball and then spring back to form a ball and socket hinge joint.

9. A holding device for use with a patient during an X-ray procedure as recited in claim 7, wherein said one of a ball and a socket on said proximal edge is a ball.

10. A holding device for use with a patient during an X-ray procedure as recited in claim 7, and further comprising an elongated arm having a proximal end and a distal end and a mating element at said distal end that mates to said one of a ball and a socket on said proximal edge.

11. A holding device for use with a patient during an X-ray procedure as recited in claim 10, wherein said one of a ball and a socket on said proximal edge and said mating element at said distal end of said elongated arm form a first ball and socket joint.

12. A holding device for use with a patient during an X-ray procedure as recited in claim 11, and further comprising a second ball and socket joint on said elongated arm between said first ball and socket joint and said proximal end.

13. A holding device for use with a patient during an X-ray procedure as recited in claim 12, and further comprising an X-ray shield mounted on said arm between said handle and said retainer.

14. A holding device for use with a patient during an X-ray procedure as recited in claim 11, wherein said ball and socket joint includes a ball element and flexible arms that form a socket, wherein the flexible arms flex outwardly as the ball element is pushed into the socket and then spring back to wrap more than half-way around the ball element in order to retain the ball element in the socket.

\* \* \* \* \*